United States Patent
MacDonald (10) Patent No.: US 7,340,304 B2
(45) Date of Patent: Mar. 4, 2008

(54) BIOTHERMAL POWER SOURCE FOR IMPLANTABLE DEVICES

(75) Inventor: Stuart G. MacDonald, Pultneyville, NY (US)

(73) Assignee: Biomed Soutions, LLC, Pittsford, NY (US)

( * ) Notice: Subject to any disclaimer, the term of this patent is extended or adjusted under 35 U.S.C. 154(b) by 138 days.

(21) Appl. No.: 10/939,898

(22) Filed: Sep. 13, 2004

(65) Prior Publication Data

US 2005/0038483 A1 Feb. 17, 2005

Related U.S. Application Data (63) Continuation of application No. 10/694,548, filed on Oct. 27, 2003, now abandoned, which is a continuation-in-part of application No. 10/098,821, filed on Mar. 15, 2002, now Pat. No. 6,640,137.

(51) Int. Cl.
- *A61N 1/362* (2006.01)
- *A61N 1/375* (2006.01)
- *A61M 5/00* (2006.01)

(52) U.S. Cl. ............... 607/35; 607/116; 604/891.1
(58) Field of Classification Search ............ 607/34–36, 607/116; 60/641.6; 438/54–55; 136/205, 136/211–212; 604/891.1
See application file for complete search history.

(56) References Cited

U.S. PATENT DOCUMENTS

| | | | |
|---|---|---|---|
| 3,623,817 A | 11/1971 | Celio | |
| 3,648,152 A | 3/1972 | Low | |
| 3,700,028 A * | 10/1972 | Noren | .......................... 165/272 |
| 3,780,425 A | 12/1973 | Penn | |
| 3,781,176 A | 12/1973 | Ade | |
| 3,818,304 A | 6/1974 | Hursen et al. | |
| 4,014,346 A | 3/1977 | Brownlee | |
| 4,019,364 A | 4/1977 | Maddox | |
| 4,026,726 A | 5/1977 | Carney | |
| 4,032,363 A * | 6/1977 | Raag | .......................... 136/211 |
| 4,095,998 A | 6/1978 | Hanson | |
| 4,422,146 A | 12/1983 | Yamaguchi | |
| 4,432,363 A * | 2/1984 | Kakegawa | .................... 607/33 |
| 4,505,427 A | 3/1985 | Bridges | |
| 4,938,244 A | 7/1990 | Kumada | |
| 5,073,758 A | 12/1991 | Postlewait | |
| 5,137,927 A | 8/1992 | Wolff | |
| 5,241,828 A | 9/1993 | Kapitulnik | |
| 5,403,792 A | 4/1995 | Kita | |
| 5,439,528 A | 8/1995 | Miller | |
| 5,446,437 A | 8/1995 | Bantien | |

(Continued)

FOREIGN PATENT DOCUMENTS

| | | | |
|---|---|---|---|
| WO | WO 00/09201 | * | 2/2000 |

*Primary Examiner*—Mark Bockelman (57) ABSTRACT

An implantable, rechargeable assembly comprised of an implantable device disposed within a living organism, an electrical storage device connected to the implantable device, and a thermoelectric charging assembly operatively connected to the electrical storage device. The thermoelectric charging assembly has devices for transferring thermal energy between the living organism and a thermoelectric module, for generating an electrical current from the thermal energy, for charging the electrical storage device with the electrical current, for determining the extent to which the electrical storage device is being charged with the electrical current, and for generating a signal whenever the extent to which the electrical storage device is being charged with the electrical current falls below a specified value.

12 Claims, 6 Drawing Sheets

U.S. PATENT DOCUMENTS

| | | |
|---|---|---|
| 5,491,452 A | 2/1996 | Ohtsubo |
| 5,507,879 A | 4/1996 | Gyoten |
| 5,517,468 A * | 5/1996 | Inoue et al. .................. 368/64 |
| 5,522,856 A | 6/1996 | Reineman |
| 5,532,284 A | 7/1996 | Bartlett |
| 5,565,763 A | 10/1996 | Attendale |
| 5,697,956 A | 12/1997 | Bornzin |
| 5,708,371 A | 1/1998 | Koyama |
| 5,742,471 A | 4/1998 | Barbee, Jr. |
| 5,784,401 A | 7/1998 | Suzuki |
| 5,827,326 A | 10/1998 | Kroll |
| 5,869,892 A | 2/1999 | Ohtsubo |
| 5,897,330 A | 4/1999 | Watanabe et al. |
| 5,900,447 A | 5/1999 | Ishida |
| 5,952,837 A | 9/1999 | Koyama |
| 5,957,956 A | 9/1999 | Kroll |
| 5,993,996 A | 11/1999 | Firsich |
| 6,015,630 A | 1/2000 | Padture |
| 6,067,473 A | 5/2000 | Greeninger |
| 6,078,183 A | 6/2000 | Cole, Jr. |
| 6,108,579 A | 8/2000 | Snell |
| 6,160,042 A | 12/2000 | Ishida |
| 6,207,886 B1 | 3/2001 | Kusakabe |
| 6,207,887 B1 | 3/2001 | Bass |
| 6,232,907 B1 | 5/2001 | Nagaraj |
| 6,252,762 B1 | 6/2001 | Amatucci |
| 6,255,376 B1 | 7/2001 | Shikata |
| 6,269,266 B1 | 7/2001 | Leysieffer |
| 6,470,212 B1 | 10/2002 | Weijand |
| 6,631,072 B1 | 10/2003 | Paul |
| 6,640,137 B2 | 10/2003 | MacDonald |
| 6,660,926 B2 * | 12/2003 | Fleurial et al. ............. 136/203 |
| 2004/0093041 A1 | 5/2004 | MacDonald |
| 2004/0150298 A1 | 8/2004 | Styblo |
| 2005/0171580 A1 | 8/2005 | MacDonald |

* cited by examiner

BIOTHERMAL POWER SOURCE FOR IMPLANTABLE DEVICES

CROSS-REFERENCE TO RELATED PATENT APPLICATIONS

This application is a continuation of patent application U.S. Ser. No. 10/694,548, filed on Oct. 27, 2003, now abandoned which is a continuation-in-part of patent application U.S. Ser. No. 10/098,821, filed on Mar. 15, 2002, now U.S. Pat. No. 6,640,137, both of which are incorporated herein by reference.

FIELD OF THE INVENTION

A device for providing a permanent source of energy comprised of a thermoelectric module for creating electrical energy created by a temperature gradient in the body.

BACKGROUND OF THE INVENTION

Implantable medical devices (such as, for example, cardiac assist devices, drug infusion pumps, and pain management devices) all require electrical power to carry out functions such as pacing the heart, delivering a drug, or stimulating nerves. These devices also require electrical power for basic control functions and for communicating with other devices and with external controllers.

The use of these and other active medical implantable devices is growing in popularity as new technology enables further miniaturization and as the basic understanding of disease grows. An example of this is the recent expansion of electronic sensing and stimulation technology to applications in deep brain stimulation (DBS), which shares much of the technology developed for cardiac pacing systems and is providing relief to people suffering from Parkinson's disease and epilepsy. The expansion of applications for implantable medical devices will only accelerate in the future.

One of the early limitations to the implantation of medical electronics was the power source itself, and much development work has been done over the past forty years to improve the reliability and longevity of battery sources and to reduce the power demands of the pacemaker circuits themselves. As a result, current pacemaker batteries last several years in many applications.

In spite of these improvements in pacemaker and battery design, and especially in the case of other implantable devices that put heavy demands on their power source, one of the primary reasons for surgical removal of cardiac pacemakers, drug delivery pumps, and other implanted devices is battery lifetime. The need for surgical removal of an entire implanted device is often the result of the need to integrate the battery into the primary device case in order to eliminate corrosion thereof and the adverse health effects of leakage.

Some attempts have been made to provide a renewable power source by means of applying external power, primarily by inductive coupling of radio frequency (RF) energy to an internal, implanted antenna. However, the use of this technique is inconsistent with the use of magnetic resonance imaging (MRI), so patients with a radio-frequency rechargeable implanted device will be unable to have MRI diagnoses of potentially serious conditions. Additionally, radio-frequency induction often requires a patient to regularly set aside time for the recharging process; this is often inconvenient and frequently causes non-compliance.

The implantable devices that require such power sources are well known in the art; their power sources are often used to provide power for sensing, control, tissue stimulation, drug dispensing, external communication, and other necessary functions.

Some of the prior art improvements in such power sources are discussed below by reference to several United States patents; the entire disclosure of each of these United States patents is hereby incorporated by reference into this specification.

U.S. Pat. No. 6,108,579 illustrates some of the recently developed technology relating to such power sources. This patent discloses a battery-monitoring apparatus and method for programming of cardiac stimulating devices; the patent specifically discusses methods for tracking power usage, monitoring battery state, and displaying the estimated remaining life of the battery power source.

By way of further illustration, U.S. Pat. No. 6,067,473 discloses an implantable medical device that uses audible sound communication to provide warnings of low battery life; among the warnings provided are voiced statements warning of battery depletion.

U.S. Pat. No. 5,957,956 discloses an implantable cardioverter defibrillator (ICD) having a relatively small mass and a minimal rate of power consumption. Similarly, U.S. Pat. No. 5,827,326 discloses an implantable cardioverter defibrillator having a smaller energy storage capacity.

U.S. Pat. No. 5,697,956 discloses an implantable stimulation device having means for optimizing current drain. Similarly, U.S. Pat. No. 5,522,856 discloses a pacemaker with improved shelf storage capacity. Both of these patents describe means for minimizing the power requirements of battery power sources.

Recent emphasis on the availability of magnetic resonance imaging (MRI) diagnoses for patients has also created a focus on the inappropriateness of conducting such MRI procedures on patients who have implantable devices, such as cardiac pacemakers, installed. The electrical leads used in such implantable devices to both sense heart function and provide electrical pulses to stimulate the heart also act as antennae in the intense magnetic and radio frequency (RF) fields used in MRI procedures; the inductively coupled radio frequency energy received by such "antennae" are often sufficient to damage or destroy the pacemaker itself, and/or to create unwanted pacing of the heart, and/or to ablate blood vessels, and/or to scar sensitive heart tissue at the electrode/heart interface. Death of the patient may result, and has resulted, from one or more of these phenomena.

More recent developments in MRI technology have created the opportunity for magnetic resonance angiography (MRA), which is the use of MRI techniques that are focused on cardiac structures and function. This direct use of MRI at the heart often further exacerbates the existing difficulties in using MRI on pacemaker patients.

One solution to these problems is the subject of U.S. provisional patent application Ser. No. 60/269,817; the entire disclosure of such patent application is hereby incorporated by reference into this specification. The approach disclosed in this patent application is the use of fiber optics in place of electrical leads for pacemakers and for other implantable devices. The devices of this patent application provide means for transmission via MRI-proof optical fibers, and then re-conversion from optical to electrical pulses at the heart. In order to serve the relatively higher power demands of this optical solution to the MRI problem, either battery size must be substantially increased, or pacemaker installed life must be substantially shortened, or a means for recharging the pacemaker power source must be utilized.

By way of further illustration, U.S. Pat. No. 4,014,346 discloses a hermetically sealed cardiac pacer system and recharging system therefore. The approach taken in this patent is to use inductive coupling of external energy to recharge an internal battery. This and other similar approaches would help resolve the battery life issues discussed above, were it not for this critical issue of MRI diagnoses; the very presence of an element that can accept externally-provided radio frequency energy makes MRI compatibility for this and similar devices impossible.

Thus, there is a need to provide a power supply means for periodic recharging of an implantable device that is not susceptible to the deleterious effects of MRI and other forms of electromagnetic interference. Further, there is a need to provide this capability in a manner that does not detract from the nominal performance of the implantable device and to do so in a manner that is convenient for the patient.

It is an object of this invention to provide such an improved power supply.

SUMMARY OF THE INVENTION

In accordance with this invention, there is provided an implantable, rechargeable assembly comprised of an implantable device disposed within a living organism, an electrical storage device connected to said implantable device, and a thermoelectric charging assembly operatively connected to said electrical storage device, wherein said thermoelectric charging assembly is comprised of means for transferring thermal energy between said living organism and a thermoelectric module, means for generating an electrical current from said thermal energy, means for charging said electrical storage device with said electrical current, means for determining the extent to which said electrical storage device is being charged with said electrical current, and means for generating a signal whenever the extent to which said electrical storage device is being charged with said electrical current falls below a specified value. There is further provided such an implantable, rechargeable assembly wherein the implantable device therein is a cardiac assist device. There is further provided such an implantable, rechargeable assembly wherein the implantable device therein is a drug delivery device. There is further provided such an implantable, rechargeable assembly wherein the implantable device therein is a deep brain stimulation device.

In accordance with this invention, there is further provided an implantable, rechargeable assembly comprised of an implantable device disposed within a living organism, a line for connecting said implantable device to an electrical storage device, a thermoelectric charging assembly, a line for operatively connecting said thermoelectric charging assembly to said electrical storage device, wherein said thermoelectric charging assembly is comprised of means for transferring thermal energy between said living organism and a thermoelectric module, means for generating an electrical current from said thermal energy, means for charging said electrical storage device with said electrical current, means for determining the extent to which said electrical storage device is being charged with said electrical current, and means for generating a signal whenever the extent to which said electrical storage device is being charged with said electrical current falls below a specified value, and a line for operatively connecting said means for determining the extent to which said electrical storage device is being charged with said electrical current to said electrical storage device.

In accordance with this invention, there is further provided a method for increasing the thermal gradient that is present at an implantable power device implanted in a living organism, said power device comprising an electrical storage device and a thermoelectric module having a first surface at a first temperature and a second surface at a second temperature, wherein said method comprises the steps of monitoring at least one condition that may indicate the necessity of increasing said thermal gradient; performing a decision to increase said thermal gradient based upon said monitoring of said at least one condition; and performing at least one action to cause a change in temperature of at least one of said first surface and said second surface.

BRIEF DESCRIPTION OF THE DRAWINGS

The invention will be described by reference to the specification and to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENTS

Figure 1:
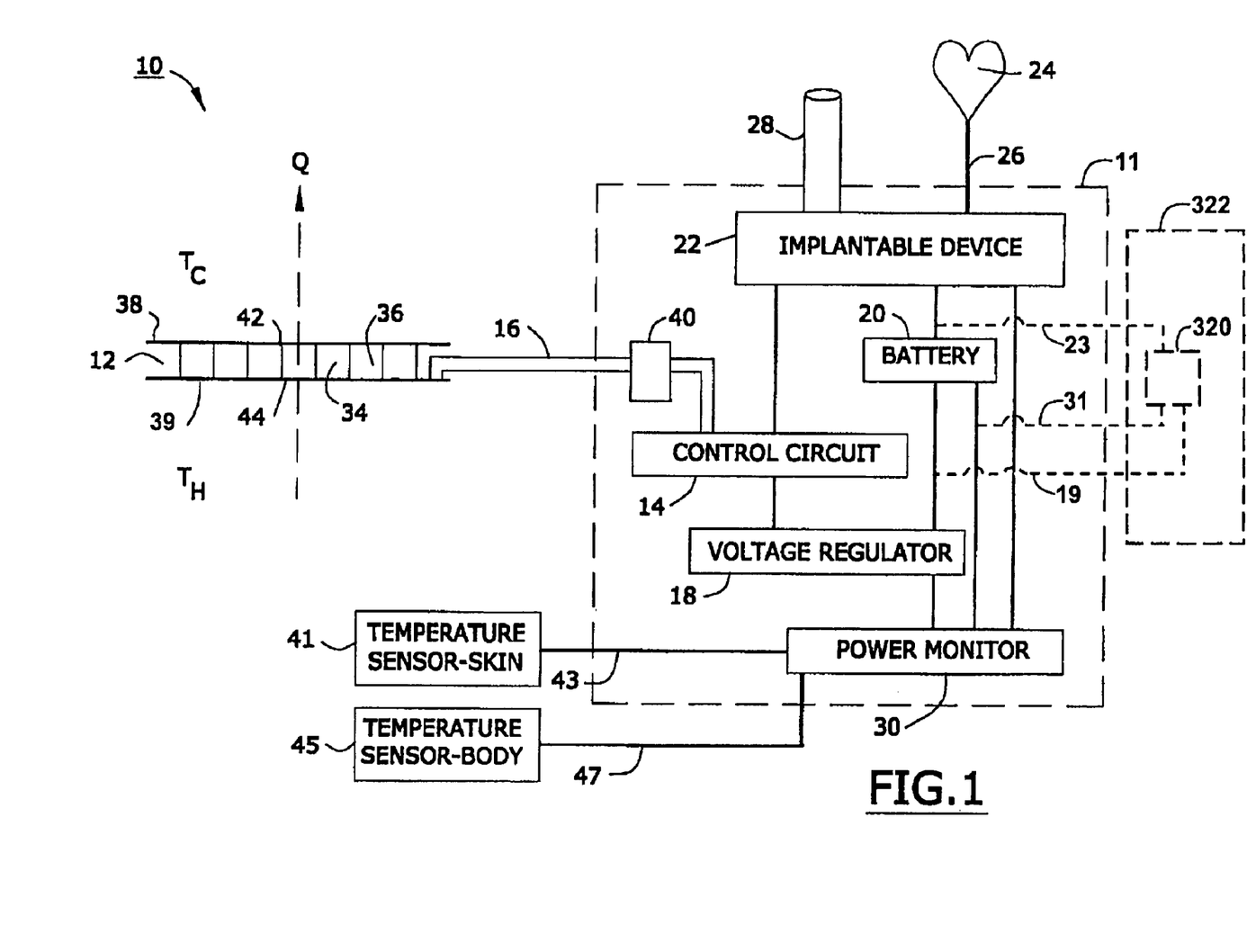
FIG. 1 is a schematic diagram of a preferred of one preferred biothermal power system of this invention.

FIG. 1 is a block diagram of a preferred biothermal power system 10. In the preferred embodiment depicted in FIG. 1, device 10 works on the Seebeck effect.

The Seebeck effect is the development of a voltage due to differences in temperature between two junctions of dissimilar metals. Reference may be had, e.g., to U.S. Pat. No. 5,565,763 (thermoelectric method and apparatus), U.S. Pat. No. 5,507,879 (sensor using thermoelectric materials), U.S. Pat. No. 4,019,364 (method of testing welds by using the Seebeck effect), U.S. Pat. No. 3,648,152 (Seebeck effect compensation), U.S. Pat. No. 6,207,886 (Skutterudite thermoelectric material), U.S. Pat. Nos. 6,078,183, 5,952,837, 5,869,892, 5,784,401, 5,708,371, 5,491,452 (Peltier element as series noise clamp), U.S. Pat. Nos. 5,446,437, 5,439,528 (laminated thermo element), U.S. Pat. Nos. 5,241,828, 5,073,758, 4,938,244, 4,505,427, 4,095,998 (thermoelectric voltage generator), U.S. Pat. No. 4,026,726, and the like. The entire disclosure of each of these United States patents is hereby incorporated by reference into this specification.

Referring again to FIG. 1, thermoelectric module 12 is connected to and provides electrical current to control circuit 14 by means of leads 16. Control circuit 14, in turn, is operatively connected to a voltage regulator 18. The voltage regulator 18 provides direct current to battery 20, which, in turn, provides power to the implantable device 22. In the preferred embodiment depicted in FIG. 1, implantable device 22 is capable of providing stimulation to an organ (such as a human heart) 24 via leads 26. The leads 26 may either be electrical leads, and/or optical leads.

The implantable device 22 also is capable of providing material (such as, e.g., a therapeutic or stimulatory drug, or a hormone) via conduit 28 to one or more sites in a living organism (not shown). Thus, e.g., such conduit 28 may be caused to deliver an irritant that will cause tissue within said living organism to increase its local temperature. Alternatively, or additionally, when a patient becomes aware that the temperature differential used to power device 10 is not sufficient, he can topically apply some of the irritant material to some of his tissue.

Power monitor 30 is operatively connected to battery 20 and, by means of one or more suitable sensors, detects the power level of such battery 20. The power monitor 30 is also operatively connected to the implantable device 22. In one preferred embodiment, the implantable device 22 is capable of providing a warning to either the patient and/or his physician whenever the power being furnished to such device is inadequate. By way of illustration, one may use the warning system depicted in U.S. Pat. No. 6,067,473 that uses audible sound communication to provide warnings of low battery life; the entire disclosure of such United States patent is hereby incorporated by reference into this specification. Alternatively, or additionally, one may use the battery-monitoring device of U.S. Pat. No. 6,108,579, which provides a display of the remaining life of the battery; the entire disclosure of this United States patent is hereby incorporated by reference into this specification.

The battery 20 preferably is a rechargeable battery. Alternatively, or additionally, other electrical storage devices also may be used. Thus, e.g., one may use a capacitive storage device constructed of carbon or other nanomaterials, or a hybrid device. Such devices are disclosed e.g., in U.S. Pat. No. 6,252,762 ("Rechargeable hybrid battery/supercapacitor system"); U.S. Pat. No. 5,993,996 ("Carbon supercapacitor electrode materials"); U.S. Pat. No. 6,631,072 ("Charge storage device"); and U.S. Pat. No. 5,742,471 ("Nanostructure multilayer dielectric materials for capacitors and insulators"). The disclosures of each of these United States patents are incorporated herein by reference.

In a further embodiment, system 10 is provided without battery 20, and instead, system 10 is operatively connected to a battery or other electrical storage device in a second implanted device such as e.g., a pacemaker. Referring to FIG. 1, second implanted device 322 comprises battery 320 or other electrical storage device 320. Power system 10 comprises primary device 11, which is provided without battery 20 other electrical storage device 20. Instead, battery 320 of second implanted device 322 is connected to power monitor 30, to implantable device 22, and to voltage regulator 18 via lines 31, 23, and 19, respectively. (As used herein, a "line" is a strand of material that conducts electrical current, such as e.g., a metal wire.) In this manner, the energy generated by system 10 is stored in battery 320, and subsequently used by implanted devices 22 and 322.

Referring again to FIG. 1, and in the preferred embodiment depicted therein, it will be seen that electrical leads 16 first communicate with polarity reverser 40 prior to the time they are connected with the control circuit 14. As will be apparent, if the temperature ($T_c$) on surface 42 of thermoelectric module 12 is higher than the temperature ($T_h$) on surface 44 of the thermoelectric module 12, then the polarity of the electric current produced in such a situation will be the reverse of the situation than when the temperature $T_c$ is lower than temperature $T_h$. Absent a polarity reversal device, electrical current will not effectively flow into the control circuit under all conditions of temperature.

The polarity reversal device 40 may be any of the means for reversing polarity known to those skilled in the art. Reference may be had, e.g., to U.S. Pat. Nos. 6,232,907, 3,821,621, 4,422,146, 3,623,817, and the like. The entire disclosure of each of these United States patents is hereby incorporated by reference into this specification.

Figure 2:
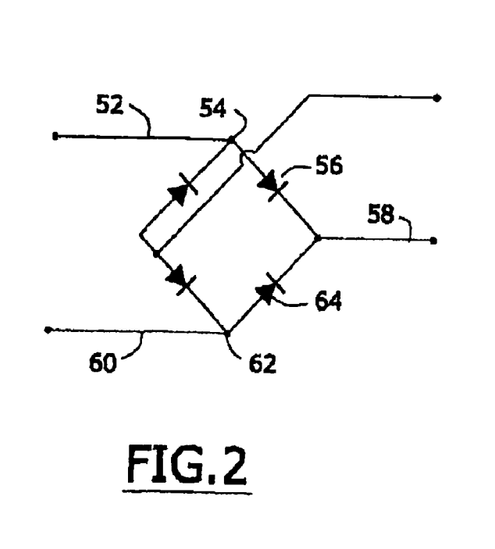
FIG. 2 is a polarity reversing device that may be used in the power system of FIG. 1.

FIG. 2 is a schematic diagram of one preferred polarity reversal device 50 that may be used. Referring to FIG. 2, when lead 52 is negative, electrons flow to point 54, and then through diode 56, and then through line 58. When, however, the polarity is reversed due to a change in the temperatures of surfaces 42 and 44 (see FIG. 1), electrons will flow through line 60, through to point 62, through diode 64, and then through line 58. Thus, regardless of whether $T_c$ is higher or lower than $T_h$, the temperature difference between them will cause power generation. This feature is especially advantageous when the ambient conditions are fluctuating and/or when the body temperature near the device 10 is especially low or high.

Figure 3:
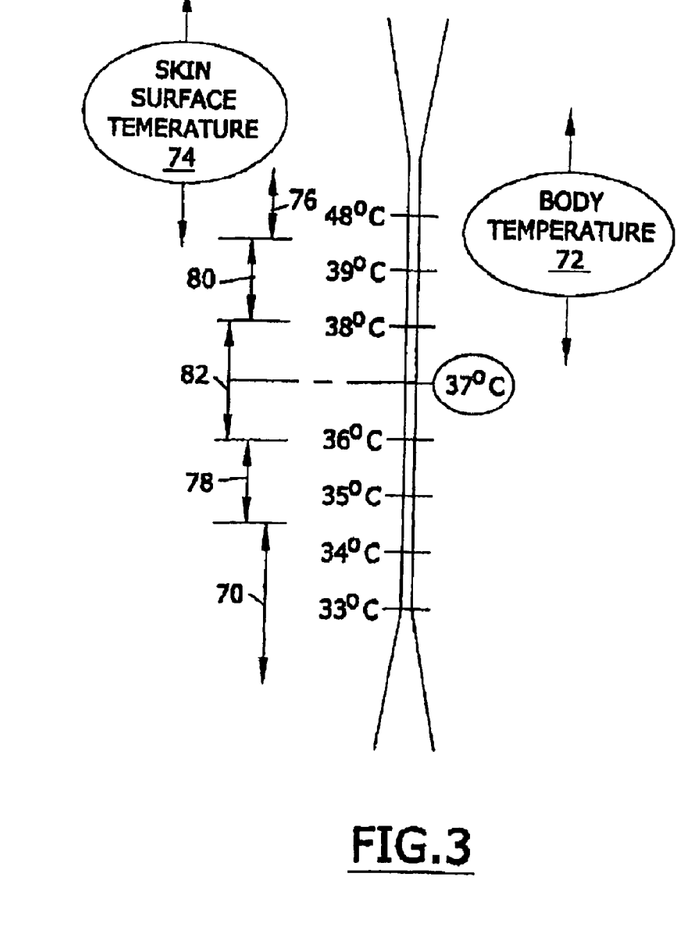
FIG. 3 is a diagrammatic representation of the efficacy of the device of this invention at different ambient temperatures.

FIG. 3 is graph of the multiple situations that may occur as $T_c$ and $T_h$ vary. Referring to FIG. 3, and in zone 70, the body temperature 72 is substantially higher than the skin surface temperature 74. Because of this positive temperature differential, and referring to FIG. 2, electrons will flow through line 52, to point 54, through diode 56, and then through line 58. Furthermore, inasmuch as the temperature differential in zone 70 is generally greater than 2 degrees Celsius, a plentiful supply of electrical energy will be produced and supplied to the control circuit 14 (see FIG. 1).

By comparison, and referring again to FIG. 3, in zone 76 the skin surface temperature 74 is substantially higher than the body temperature 72. Because of this negative temperature differential, electrons will flow through line 60, to point 62, through diode 64, and then to line 58 (see FIG. 2). Again, because the temperature differential in this zone is generally greater than 2 degree Celsius, a generous supply of electrons will flow to control circuit 14.

In intermediate zones 78 and 80, however, the temperature differential may only be 1 degree Celsius. However, this one-degree positive or negative temperature differential still is sufficient to provide adequate electron flow to control circuit 14.

However, in zone 82, the temperature differential between the surfaces 44 and 42 of module 12 often are less than 1 degree Celsius. In this zone, the current flow is often inadequate to power the implantable device 22. In this case, battery 20 will, over sufficient time, tend to discharge.

In zones 70, 76, 78, and 80, the device 10 will continually charge battery 20 through means of, e.g., voltage regulator 18; and the amount of electrical charge imparted to battery 20 will exceed the drain on such battery caused by implanted device 22.

However, in zone 82, the amount of electrical charge imparted to battery 20 will be less than the drain on such battery caused by the needs of implanted device 22. If such a situation persists for a long period of time, the battery 20 will become discharged and have to be replaced with a new battery.

In order to avoid the need to frequently subject a patient to surgery, the device 10 of this invention substantially extends battery life. One means of so doing is to provide a warning to the patient whenever the zone 82 conditions occur for a sustained period of time.

Referring again to FIG. 1, a temperature sensor 41 senses the temperature outside the living organism, preferably at or through the surface of the organism's skin. This information is conveyed, via lines 43, to power monitor 30.

A second temperature sensor, sensor 45, senses the temperature of the living organism and provides such information, via lines 47, to the power monitor 30. Thus, at all times, the power monitor can determine the difference between the temperature on surfaces 42 and 44, the direction of such temperature difference, and the amount of time such temperature difference has existed.

Power monitor 30 preferably is comprised of means for measuring the rate of current flow into battery 20. In the preferred embodiment depicted in FIG. 1, this information is provided to power monitor 30 by voltage regulator 18. Furthermore, because the power monitor 30 is connected to the battery 20, it also is continually aware of the charge status of the battery 20.

Armed with this information, and preferably using an algorithm that may be periodically modified as necessary upon command from implantable device 22, the power monitor can cause the implantable device 22 to emit a warning signal. Implantable devices capable of emitting warning signals have been described elsewhere in this specification.

When such a warning signal has been produced by the implantable device, the patient then has the opportunity to increase the temperature differential between surfaces 44 and 46. He may so do by either putting on more clothing, taking off some clothing, and/or moving to a warmer or cooler environment.

Referring again to FIG. 1, and in the preferred embodiment depicted therein, it is preferred that thermoelectric module 12 define " . . . a hot side and a cold side, said module comprising: A) a plurality of P-type thermoelectric elements, B) a plurality of N-type thermoelectric elements, said P-type elements and said N-type elements being arranged in an array and insulated from each other with self adhering polyimide film, C) a plurality of contacts on said cold side and said hot side connecting said elements in an electric circuit." This particular module is described and claimed in U.S. Pat. No. 6,207,887; the entire disclosure of this United States patent is hereby incorporated by reference into this specification.

One may use thermoelectric modules, similar to those disclosed in U.S. Pat. No. 6,207,887, but which use different separator elements between the P-type and the N-type elements. Thus, e.g., one may utilize epoxy-impregnated paper isolators; see, e.g., U.S. Pat. Nos. 3,780,425 and 3,781,176, the entire disclosures of each of which is hereby incorporated by reference into this specification.

In one embodiment, a sufficient number of such P-type and N-type elements of such U.S. Pat. No. 6,207,887 are utilized to provide a device 10 that, with a temperature differential between $T_h$ and $T_c$ of only 2 degree Celsius, will produce at least 50 microwatts of electrical power at a voltage of from about 0.3 to about 0.5 volts d.c. In another embodiment, the device produces at least 100 microwatts of power at such voltage of from 0.3 to about 0.5 volts when presented with a temperature differential of 1 degree Celsius.

In one embodiment, illustrated in FIG. 1, the thermoelectric module 12 will have a substantially square shape, a length of from about 1.3 to about 1.7 inches, and a thickness of from about 0.2 to about 0.3 inches.

Referring again to FIG. 1, and in the preferred embodiment depicted therein, it will be seen that thermoelectric module 12 is preferably comprised of a multiplicity of n-doped/p-doped thermocouple pairs (34/36) preferably electrically arranged in series and sandwiched between ceramic plates 38 and 39.

Figure 4:
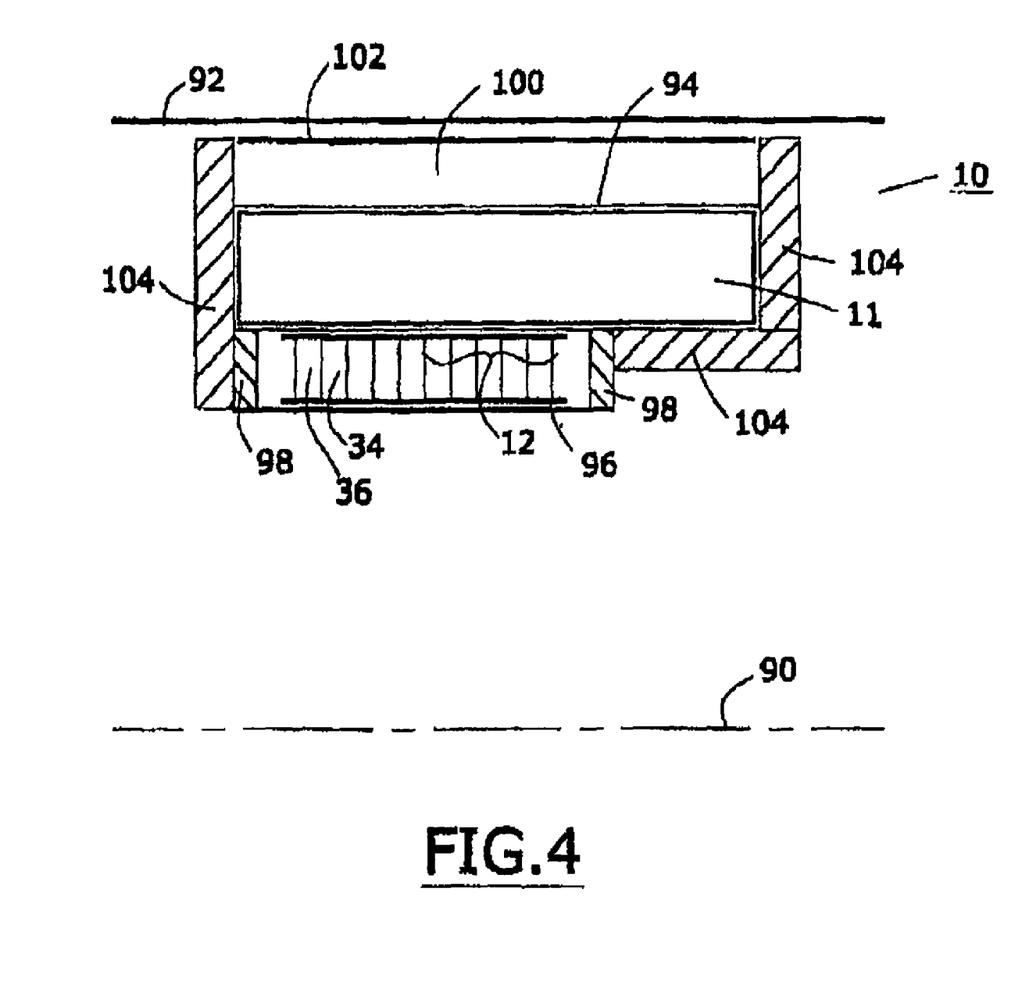
FIG. 4 is a schematic of one preferred device of this invention.

FIG. 4 is a schematic representation of the device 10 from which some unnecessary detail has been omitted for the sake of simplicity of representation. In the preferred embodiment depicted therein, the device 10 utilizes the thermoelectric module 12 described in FIG. 1, generating electrical power from the temperature gradient between the body centerline 90 and the surface of the skin 92 via the Seebeck Effect. In most cases the body core temperature is higher that the skin surface temperature, but even in cases where this relationship is temporarily reversed, control circuit 14 (see FIG. 1) will reverse polarity of its voltage regulator so that battery charging will continue.

Referring again to FIG. 4, implant device 10 comprises a primary case 94 that houses the primary device. In the embodiment depicted, primary device 11 is comprised of a controller circuit 14 (not shown, but see FIG. 1), a voltage regulator 18 (not shown, but see FIG. 1), a power monitor 30 (see FIG. 1), a battery 20 (see FIG. 1), a polarity reversal unit 40 (see FIG. 1), and an implantable device 22 (see FIG. 1).

In the embodiment depicted, case 94 provides a hermetic seal around all components, provides for passage of lead wires without violating hermetic seal, and further has specific thermal characteristics. In this embodiment, case 94 is preferably formed of a titanium/silver bilayer, wherein the titanium provides a robust and biocompatible outer layer, and the silver provides a highly thermally conductive inner layer.

As will be apparent, a variety of combinations of other materials, thickness, and fabrication methods may be used to derive the desired combination of strength, magnetic impermeability, biocompatibility, and high thermal conductivity.

Referring again to FIG. 4, the thermal conversion module 12 is preferably disposed immediately against the device case 94 and is in intimate thermal contact therewith, either by silver solder, brazing, conductive grease, or other means. Electrical leads from module 12 preferably pass through case 94 via hermetic means. Conductive plate 96 is preferably affixed in similar manner to the opposite surface of module 12. Ceramic insulating seal 98 surrounds module 12 and provides thermal isolation between case 94 and conductive plate 96; it and also provides a hermetic seal surrounding the module 12 to protect it from the body environment. Thus, ceramic insulating seal 98 should preferably be made from a specialized material.

One of such specialized ceramic insulating materials is disclosed in U.S. Pat. No. 5,403,792, which describes a low thermal conductivity ceramic and process for producing the same. This material comprises a sialon (Si—Al—O—N) in combination with one or more of elements La, Dy, Ce, Hf, and Zr. This material is highly rigid, impermeable, and has low thermal conductivity. The entire disclosure of this United States patent is hereby incorporated by reference into this specification.

By way of further illustration, U.S. Pat. No. 6,015,630 discloses a ceramic thermal barrier coating disposed on the metal substrate or on the optional metallic bond coat, wherein the YAG-based ceramic thermal barrier coating is selected from the group consisting of $Y_3^C Al_2^A Al_3^D O_{12}$, wherein C, A, and D are sites on the crystal structure, and further wherein all or part of the $Al^{3+}$ on the A sites, D sites, or A and D sites are substituted in an amount effective to provide the YAG-based ceramic thermal barrier coating with a thermal conductivity less than or equal to about 3 $Wm^{-1} K^{-1}$ at about 1000° C., an oxygen diffusivity less than or equal to about $10^{-15}$ $m^2 s^{-1}$ at about 1000° C., a thermal coefficient of expansion greater than or equal to about $9 \times 10^{-6}$ $°C.^{-1}$, a maximum temperature capability greater than or equal to about 1400° C., a hardness greater than or equal to about 14 GPa, an elastic modulus less than or equal to about 280 GPa, or a density less than or equal to about 6.4 $gcm^{-3}$. The entire disclosure of this United States patent is hereby incorporated by reference into this specification.

Referring once again to FIG. 4, and in the preferred embodiment depicted therein, a layer of conformable gel or polymer 100 preferably is disposed immediately above device case 94, and a conductive sealing membrane 102 serves to contain polymer/gel 100. In this preferred embodiment, the aforementioned materials provide a highly thermally conductive path from device case 94 to the skin surface 92 which is immediately above the sealing membrane 102 but which also provides for high degree of comfort for the patient. Materials for polymer/gel 100 and membrane 102 are preferably chosen to be biocompatible and also to have the appropriate flexibility and thermal conductivity.

By way of yet further illustration, U.S. Pat. No. 6,255,376 discloses a thermally conductive compound that comprises 15 to 60 volume percent of thermoplastic carrier resin consisting of a copolymer of a plasticizer with ethylene or of a polymer of the plasticizer, polyethylene and the copolymer, 40 to 85 volume percent of thermally conductive filler particles dispersed in the carrier resin, and 0.5 to 5 weight percent (for the filler particles) of a dispersing agent having (a) hydrophilic group(s) and (a) hydrophobic group(s). The thermally conductive compound has a high thermal conductivity and a plasticity in the range of temperatures of −40 to 50° Celsius. The entire disclosure of this United States patent is hereby incorporated by reference into this specification.

Likewise, U.S. Pat. No. 6,160,042 discloses a method for forming a low viscosity high thermal conductivity polymer composite containing particles of hexagonal boron nitride comprising the steps of: (a) treating the surface of the hexagonal boron nitride particles with 1,4-phenylene diisocyanate, (b) thereafter reacting the thus-treated boron nitride particles with a compound of the formula $H_2 N—X—Y$. And further, U.S. Pat. No. 5,900,447 discloses a composition and method for forming a high thermal conductivity polybenzoxazine-based material. The composition comprises at least one benzoxazine resin and a filler material that includes particles of boron nitride in an amount sufficient to establish a thermal conductivity of between about 3 W/mK and 37 W/mK in the polybenzoxazine-based material. These and other like materials may be used for membrane 102 and polymer 100 shown in FIG. 4. The entire disclosure of U.S. Pat. Nos. 6,160,042 and 5,900,447 are hereby incorporated by reference into this specification.

Referring again to FIG. 4, insulating sheath 104 is preferably a flexible polymeric insulating material that surrounds the primary device case 94, further thermally isolating it from its lateral environment and, thus, encouraging the primary heat flow to be through the thermal conversion module 12, thence through the device case 94, through the conductive polymer 100, conductive membrane 102, and through the skin 92. Insulating sheath 104 may be made from a variety of biocompatible closed cell foam materials. One such material is disclosed, e.g., in U.S. Pat. No. 5,137,927 as a composite foam of low thermal conductivity comprises a) 20-80% by volume of silica aerogel particles having a mean diameter of from 0.1 to 20 mm and a density of from 0.08 to 0.40 g/cm³, b) 20-80% by volume of a styrene polymer foam which surrounds the particles of component a) and binds them to one another and has a density of from 0.01 to 0.15 g/cm³, and, if desired, c) conventional additives in effective amounts. Another such material is disclosed in U.S. Pat. No. 5,532,284 as an improved closed cell polymer foam and foaming agent involving the use of a halocarbon blowing agent (e.g., HCFC-22, HCFC-123, HCFC-123a, and HCFC-141b) in combination with an effective amount of a gas barrier resin (e.g., an ethylene/vinyl acetate copolymer, ethylene/acrylic ester copolymer or acrylic ester polymer) uniformly dispersed in the continuous polymeric phase. The presence of the gas barrier resin is shown to significantly reduce the escape of blowing agent from and/or entry of air into the foam resulting in low thermal conductivity over a longer period of time and improved thermal insulation value. The entire disclosure of these United States patents is hereby incorporated by reference into this specification.

Figure 5:
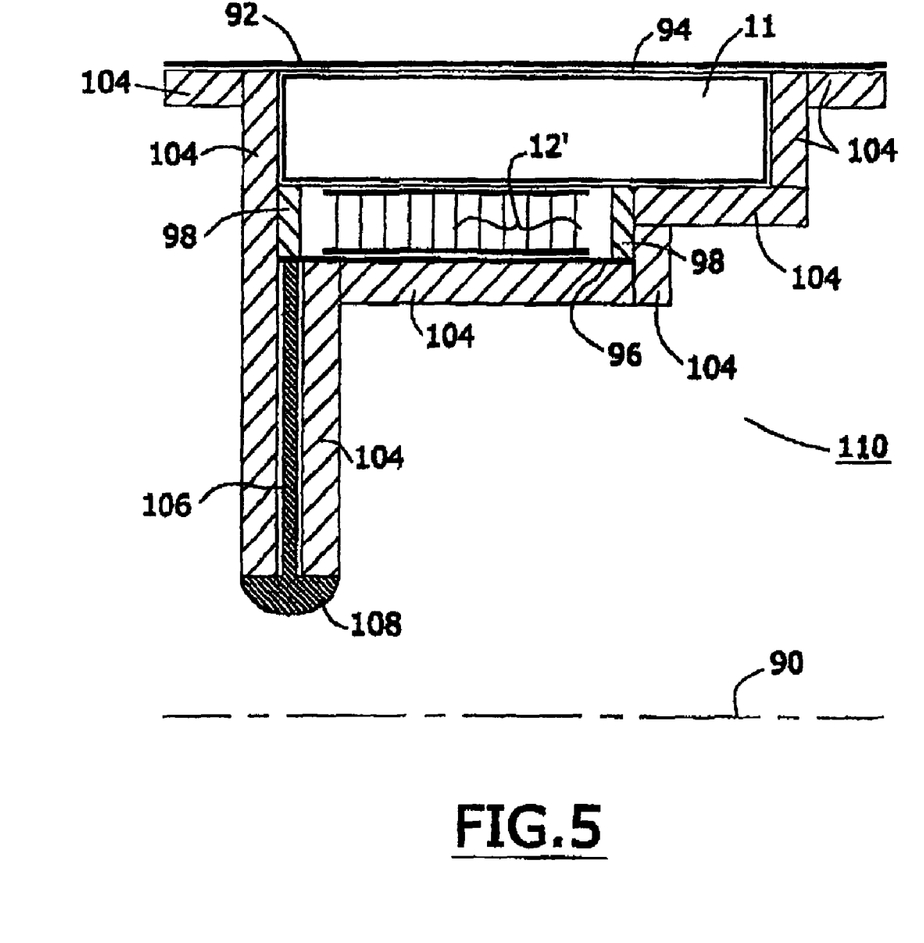
FIG. 5 is a schematic of a second preferred device of this invention.

FIG. 5 is a schematic design of a second preferred device 110. In the embodiment depicted, the temperature gradient $(T_H\text{-}T_C)$ between the body core 90 and the surface of the skin 92 provides for electrical power generation via the Seebeck Effect. Many of the components and materials are similar to those corresponding components and materials described in FIG. 4; however it will be noted that in this embodiment the conductive polymer/gel 100 and the conductive membrane 102 have been eliminated, such that the metallic case material 94 will be in direct contact with the interior surface of the skin 92. In addition, the device 110 of this embodiment has extensions of insulating sheath 104 lateral to device case 94 and immediately under the skin 92, thereby providing further thermal insulation around the power generation means and thus improving the thermal efficiency of power conversion. It will also be noted from FIG. 5 that the portion of the device 110 facing inward into the patient's body core centerline 90 has been extended in order to further enhance thermal performance by contacting a region that has a slightly higher average temperature. Conductive plate 96 is attached to another conductive member 106, shown here as an elongated rod, but which may also be a heat pipe, and which is affixed to thermal contact 108. Conductive plate 96 is also proximate to or in contact with surface 44 (see FIG. 1) of module 12, such that conductive heat transfer between surface 44 and plate 96 is rapid. Insulating sheath 104 has been extended around conductive member 106 along its length and abutting thermal contact 108 in order to provide consistent thermal isolation from the surrounding tissues and body fluids.

Conductive member 106 is oriented substantially in the direction of the temperature gradient from body core 90 to skin surface 92, thereby conducting heat into or away from plate 96, depending upon whether the difference between the temperature of body core 90 and skin 92 is positive or negative. It will be apparent therefore that the range of temperature of conductive member 106 is outside of the range in temperature defined by the temperature of surface 44 (see FIG. 1) of module 12 and surface 42 (see FIG. 1) of module 12. The geometry of this design is intended to provide for a higher temperature differential $(T_H\text{-}T_C)$ across module 12, thus providing for greater electrical power generation.

Figure 6:
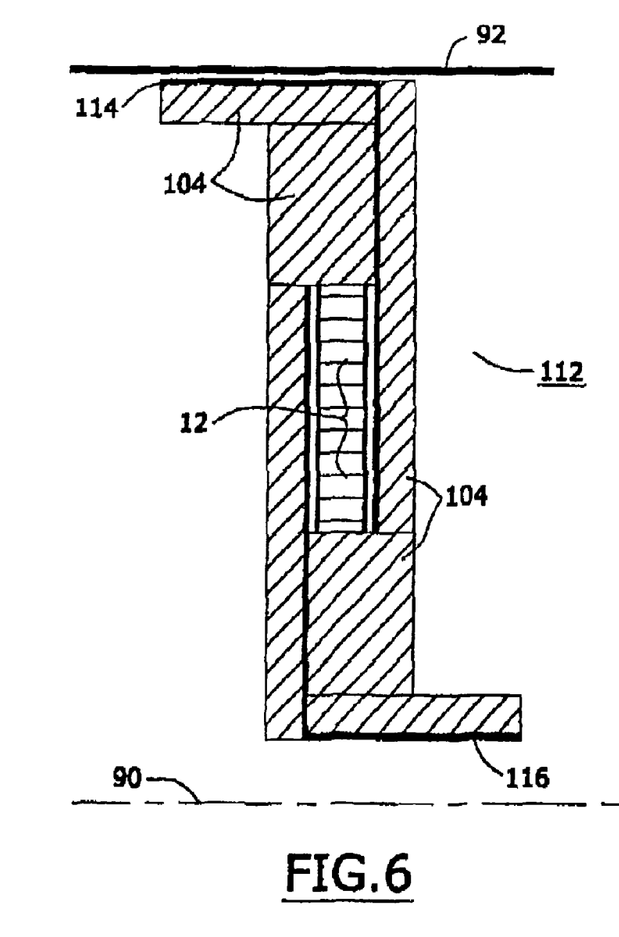
FIG. 6 is a schematic of third preferred device of the invention.

FIG. 6 is a schematic representation of a device 112 that is similar to devices 110 and 10 (see FIGS. 5 and 4), but differs therefrom in that it is oriented in a manner such that it perpendicular to the core 90; for the sake of simplicity of representation, many of the elements of such device have been omitted. In this embodiment, thermal module 12 is preferably sandwiched between a hot plate 114 (that is in immediate contact with skin surface 92) and a cold plate 116 (that extends inwardly toward the body core 90). Hot plate 114 and cold plate 116 thus extend in substantially opposite directions. Insulation 104 is used, as described hereinabove, to enhance thermal differentials.

Plate 114 is proximate to or in contact with surface 44 (see FIG. 1) of module 12, such that conductive heat transfer between surface 44 and plate 114 is rapid; and plate 116 is proximate to or in contact with surface 42 (see FIG. 1) of module 12, such that conductive heat transfer between surface 42 and plate 116 is rapid. It will be apparent that the designation of plate 114 as "hot" and plate 116 as "cold" is done for illustrative purposes, and that actions may be taken to either heat or cool skin surface 92 in order to achieve a desired temperature difference between surfaces 42 and 44 (see FIG. 1), resulting in power generation by module 12 as described previously. Such actions are described subsequently in this specification.

FIGS. 4, 5, and 6 are intended to be indicative of variations that may be designed to provide a balance between size, comfort, power efficiency, device reliability, and ease of positioning the implant within the body at various desired positions. In a further embodiment, the system 10 of FIG. 1 is configured in a manner that enables at least the thermoelectric module 12 thereof to be positioned at or near the surface of an airway. In this manner, the flow of air through the airway due to respiration will provide cooling upon surface 38 of the thermoelectric module, and since such surface will likely be maintained in a wet condition, the temperature of such surface 38 will be further reduced by evaporative cooling.

Other design features such as electrical or optical connections will be obvious to those skilled in the art, and it will also be obvious to those skilled in the art that the biothermal power generation process described herein may be scaled either up or down in size to suit power requirements of specific implantable devices. Any of the aforementioned changes may be made in the apparatus without departing from the scope of the invention as defined in the claims.

As was previously described in this specification, when the condition exists as shown in zone 82 of FIG. 3, there may not be sufficient thermal gradient present for the device of the present invention to produce sufficient electrical power for the intended use. In a further embodiment of this invention, there is provided a method for determining the necessity of increasing the thermal gradient that is present at the device, and also for increasing the thermal gradient that is present at the device if necessary, in order to increase the power generated thereby. In various embodiments, the method is performed manually or automatically by electrical stimulation of tissue, performed manually by the living body (i.e. the person or "patient") in which the device is implanted or by another person, or performed manually or automatically by chemical stimulation (irritation) of tissue.

Figure 7:
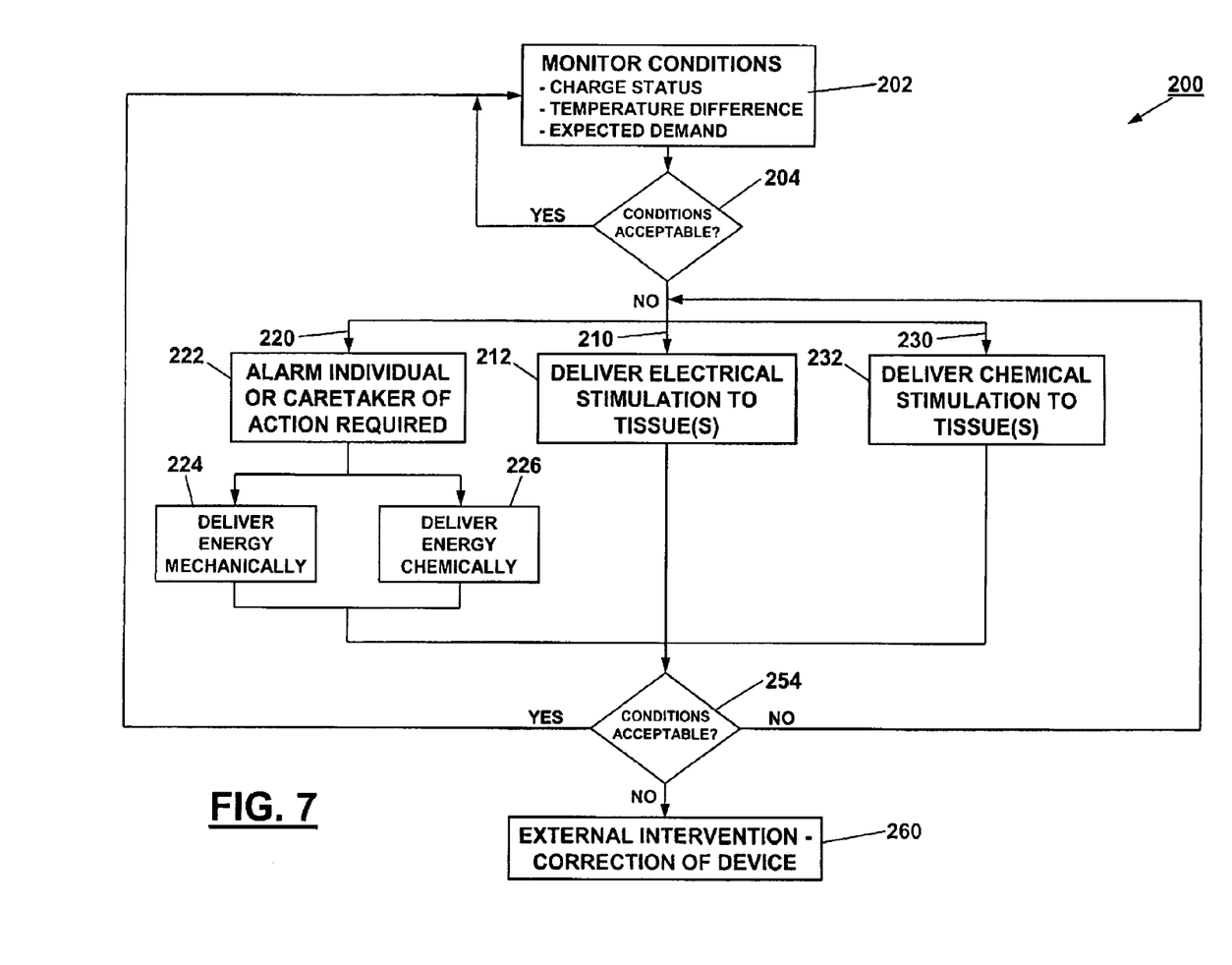
FIG. 7 is a flowchart depicting a method of the present invention for a method for increasing the thermal gradient that is present at a power device of the present invention.

FIG. 7 is a flowchart of a generalized method to increase the thermal gradient that is present at a power device of the present invention. Referring to FIG. 7, method 200 comprises the step 202 of the ongoing monitoring of conditions that may indicate the necessity of increasing the thermal gradient that is present at the device. Referring also to FIG. 1, such conditions may include the status of the battery 20, capacitive device, or other electrical energy storage device within or external to the power system 10; the temperature difference $(T_h-T_c)$ or gradient present at the thermoelectric module 12 of the power device; and the expected energy demand by the device(s) 22 powered by the system 10. Monitoring step 202 is preferably performed by power monitor 30, the capabilities of which have been previously described in this specification.

Referring again to FIG. 7, power monitor 30 is further provided with the capability to perform decision step 204 on a substantially continuous basis. If system and ambient conditions are acceptable ("YES"), monitoring step 202 continues. If system and ambient conditions are unacceptable ("NO"), power monitor 30 triggers corrective action. Such corrective action may be the provision of an alarm to the patient or other person to manually perform corrective steps, or such corrective action may be the automatic execution of corrective steps.

An example of one unacceptable system condition is where the storage device 20 is below a desired threshold value of total energy content. An example of another unacceptable system condition is where the storage device 20 is discharging at an unacceptably high rate, i.e. the power being delivered in from module 12 is so much less than the power being consumed by implantable device 22, that the storage device will become depleted in an unacceptably short time if corrective action is not taken. An example of an unacceptable ambient condition is where the absolute value of the temperature difference between surface 42 and surface 44 of thermoelectric module 12 (i.e. $|T_h-T_c|$) has decreased below a threshold value, such that thermoelectric module is not producing a sufficient amount of power to operate implantable device and charge battery 20. Such a condition has been previously described by way of example as zone 82 in FIG. 3.

In one embodiment, such corrective action is via path 210, comprised of the step 212 of delivering electrical stimulation to the tissue(s) that are proximate to or in contact with system 10, and in particular, thermoelectric module 12 of system 10. In one embodiment, electrical leads or contacts (not shown) are provided in contact with such tissues, and electrical impulses are delivered to such tissues therethrough. Such electrical impulses may be used to stimulate tissue such as e.g., muscle tissue, thereby causing such tissue to intermittently contract and relax. Such contraction and relaxation will increase the local temperature of such tissue. The proper selection of the location of tissue to be so stimulated will result in an increase in the temperature difference $(T_h-T_c)$ proximate to thermoelectric module 12 system 10. In the preferred embodiment, such stimulation is provided automatically in response to decision 204. However, in an alternative embodiment, an alarm may be provided to the patient or another person to provide such stimulation.

In another embodiment, in response to a "NO" answer in decision step 204, corrective action is via path 220, comprised of a first alarm step 222, in which the patient or other person is alerted of the need of corrective action required. Such corrective action may include the step 224 of delivering energy to the tissue proximate to or in contact with thermoelectric module 12 through mechanical heat transfer means, or the step 226 of delivering energy through chemical means, or both.

In step 224, such mechanical heat transfer means include heat transfer by conductive means, heat transfer by convective means, and heat transfer by radiative means, and combinations thereof. In general, the effect of such mechanical heat transfer means is preferably applied to the skin of the patient in order to produce the desired temperature gradient, and may include either a heating or a cooling of such skin.

For example, heat transfer by convective means may be achieved by the patient moving close to a convective air conditioner or space heater that is discharging a stream of conditioned air, or by using a hand-held heating device such as a blow dryer to heat the skin. Heat transfer by conductive means may be achieved by the application of ice or other cold objects to the skin, or by contact with an electrical heating pad, or by the wearing of a chemically generated heat source intended for such purposes, such as e.g., the ThermaCare® heat wrap that is sold by the Proctor and Gamble Corporation of Cincinnati, Ohio. Heat transfer by radiative means may be achieved by the patient moving close to a radiative heater that is radiating heat energy, such as an electrically powered infrared heater, a wood stove, and the like.

In the embodiment comprising step 226 of delivering energy through chemical means, such chemical means may include e.g., the topical application of some an irritant material to the patient's tissue by the patient or by another. Among the suitable irritants are those chemical substances such as menthol, which increase the blood circulation near the surface of the skin, but are not toxic to the skin or other tissues. A commercial example of such an irritants is "FLEXALL 454", distributed by Chattam, Inc. of Chattanooga, Tenn. Such irritants result in an increase in temperature at or near the surface of the skin.

In another embodiment, in response to a "NO" answer in decision step 204, corrective action is via path 230 comprised of step 232, in which chemical stimulation is delivered to the tissue proximate to or in contact with thermoelectric module 12 of FIG. 1. In the preferred embodiment, such chemical stimulation is delivered by implantable device 22, which may include a drug or chemical delivery pump or other delivery means (not shown). The substance used in such chemical stimulation may include an irritant or stimulant that results in an increase in circulation in the tissue, but is not toxic to bodily tissues.

In each of the alternate pathways 210, 220, or 230, the monitoring 202 of critical conditions described previously continues or is performed at a suitable frequency, such that decision 254 can be made. In the circumstance where the corrective action has made conditions acceptable, ("YES"), the corrective action is terminated, and monitoring 202 continues. In the circumstance where the corrective action has not made conditions acceptable, ("NO"), several options are available. In one option, the treatment of the selected path (210, 220, or 230) may be continued. In other options, one or more of the paths 210, 220, or 230 may be selected alternatively or additionally to the originally chosen path 210, 220, or 230. In the event that the conditions are not acceptable, and none of paths 210, 220, or 230 appear to be acceptable, step 260 is performed as a last resort, wherein external intervention is performed on system 10. Such intervention may include invasive surgery to repair or replace system 10.

FIG. 7 is intended to be indicative of a general method to increase the thermal gradient that is present at a power device of the present invention. It will be apparent that many additional variations may be made in the general method disclosed without departing from the scope of the invention as defined in the claims.

I claim:

1. An implantable assembly adapted to be disposed within a living organism, comprising:
    a thermoelectric module to convert thermal energy to electrical energy; and
    a pair of conductive leads, operatively connected to said thermoelectric module, for conducting said electrical energy from said thermoelectric module; and
    an implantable device receiving said electrical energy;
    said thermoelectric module including,
        a first L-shaped plate having a first surface and a second surface,
        a second L-shaped plate having a first surface and a second surface,
        a first insulating material substantially covering said first L-shaped plate, except said first surface and said second surface thereof,
        a second insulating material substantially covering said second L-shaped plate, except said first surface and said second surface thereof, and
        thermoelectric elements disposed between said second surface of said first L-shaped plate and said second surface of said second L-shaped plate;
    said first L-shaped plate and said second L-shaped plate transferring thermal energy;
    said thermoelectric elements converting thermal energy to electrical energy.

2. The implantable assembly as recited in claim 1, further comprising:
    an electrical storage device to store said electrical energy transferred by said pair of conductive leads.

3. The implantable assembly as recited in claim 2, wherein said electrical storage device is a battery.

4. The implantable assembly as recited in claim 2, wherein said electrical storage device is a capacitive storage device.

5. The implantable assembly as recited in claim 2, further comprising:
    means for determining a charged state of said electrical storage device.

6. The implantable assembly as recited in claim 2, further comprising:
    means for generating a signal when an energy content of said electrical storage device is below a predetermined level.

7. The implantable assembly as recited in claim 1, wherein said thermoelectric module produces an electrical power of at least 50 microwatts when presented with a temperature differential of 2 degrees Celsius.

8. The implantable assembly as recited in claim 1, wherein said implantable device is adapted to stimulate at least one organ within said living organism.

9. The implantable assembly as recited in claim 1, wherein said implantable device is adapted to stimulate at least one nerve within said living organism.

10. The implantable assembly as recited in claim 1, wherein said implantable device is a cardiac assist device.

11. The implantable assembly as recited in claim 1, wherein said implantable device is a drug delivery device.

12. The implantable assembly as recited in claim 1, wherein said implantable device is a brain stimulation device.

* * * * *

UNITED STATES PATENT AND TRADEMARK OFFICE
CERTIFICATE OF CORRECTION

PATENT NO. : 7,340,304 B2  Page 1 of 1
APPLICATION NO. : 10/939898
DATED : March 4, 2008
INVENTOR(S) : Stuart G. MacDonald It is certified that error appears in the above-identified patent and that said Letters Patent is hereby corrected as shown below:

Title page, item (73) Assignee: Biomed Soutions, LLC, Pittsford, NY (US) should read Biomed Solutions, LLC, Pittsford, NY (US)

Signed and Sealed this

Twenty-seventh Day of May, 2008

JON W. DUDAS
*Director of the United States Patent and Trademark Office*